United States Patent [19]

Clawson et al.

[11] 4,456,008
[45] Jun. 26, 1984

[54] RESPIRATORY APPARATUS AND METHOD

[76] Inventors: Burrell E. Clawson; James Weigl, 1833 3rd Street-C, both of Riverside, Calif. 92507

[21] Appl. No.: 417,226

[22] Filed: Sep. 13, 1982

[51] Int. Cl.³ ............................................. A61M 16/00
[52] U.S. Cl. ........................... 128/205.19; 128/205.12; 128/204.25; 128/911; 128/910
[58] Field of Search ........................ 128/203.28, 204.18, 128/204.21, 204.23, 204.24, 204.25, 205.13, 205.14, 205.15, 205.17, 205.18, 205.19, 205.24, 910, 911

[56] References Cited

U.S. PATENT DOCUMENTS

| | | | |
|---|---|---|---|
| 3,039,481 | 6/1962 | Schreiber et al. | 137/64 |
| 3,191,596 | 6/1965 | Bird et al. | 128/205.24 |
| 3,465,752 | 9/1969 | Brychta et al. | 128/204.25 |
| 3,721,239 | 3/1973 | Myers | 128/205.17 |
| 4,007,737 | 2/1977 | Paluch | 128/911 |
| 4,020,834 | 5/1977 | Bird | 128/205.12 |
| 4,265,237 | 5/1981 | Schuanbam et al. | 128/204.25 |
| 4,332,244 | 6/1982 | Levy et al. | 128/910 |
| 4,351,329 | 9/1982 | Ellestad et al. | 128/205.24 |
| 4,417,573 | 11/1983 | De Vries | 128/205.24 |

FOREIGN PATENT DOCUMENTS 2098491 11/1982 United Kingdom ........... 128/207.15

Primary Examiner—Henry J. Recla
Attorney, Agent, or Firm—Grover A. Frater

[57] ABSTRACT

An improved respiratory apparatus for conducting flow of supply and exhausted respiratory gas between a ventilator and a tracheal tube incorporates features and combinations of features, including aspiration, periodic pressure relief immediately downstream from the tracheal tube connection, coaxial flow conduits, to improve the form of pressure variations at the tracheal tube.

5 Claims, 7 Drawing Figures

U.S. Patent  Jun. 26, 1984  4,456,008
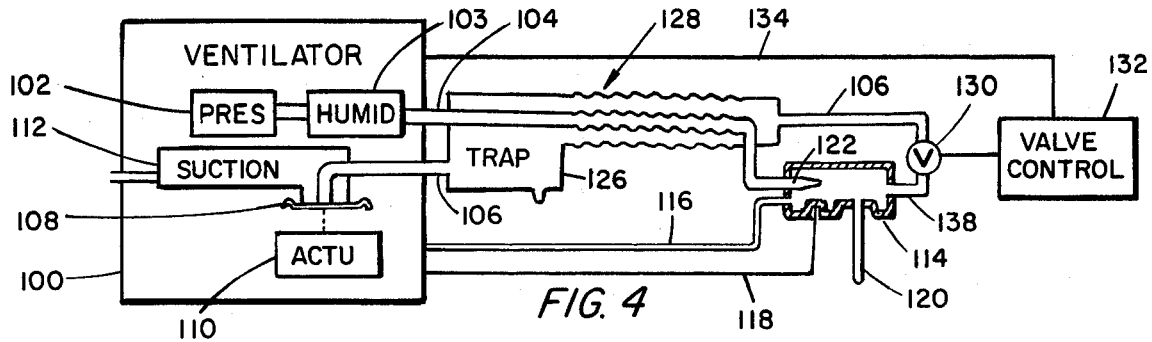
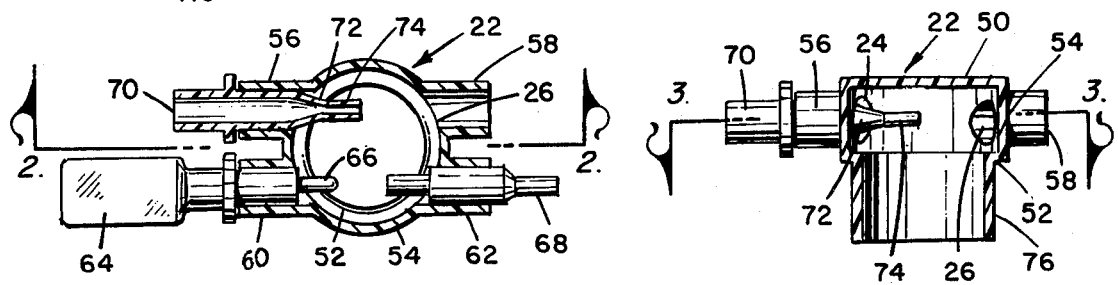
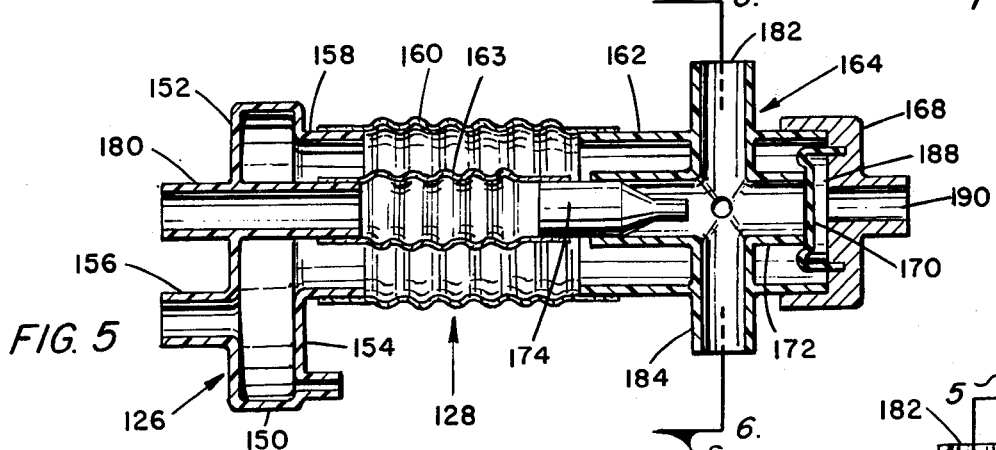
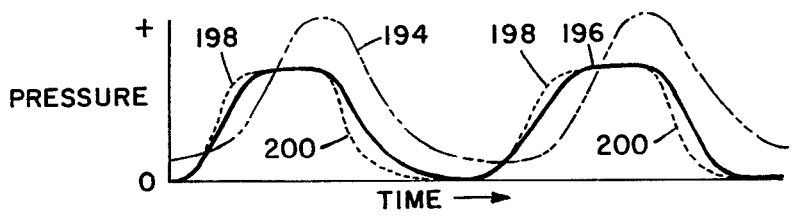
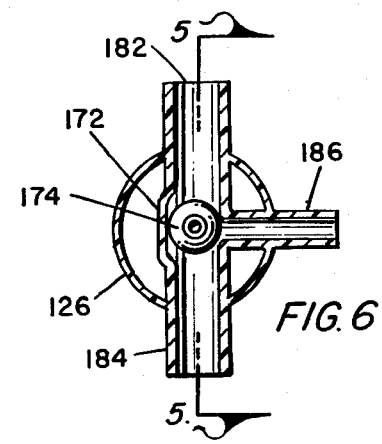
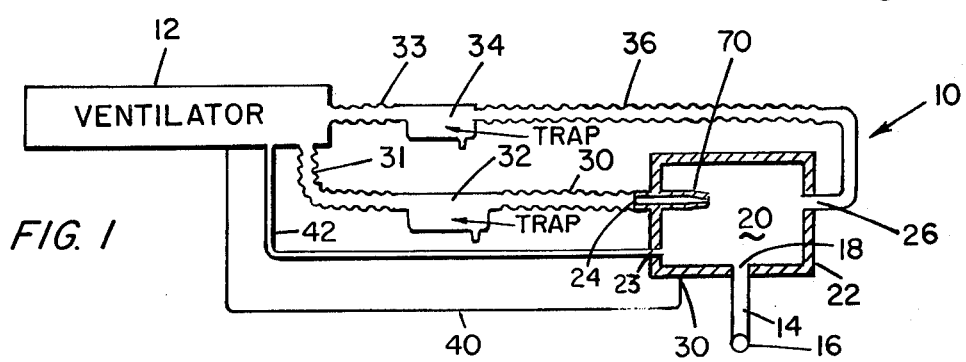

RESPIRATORY APPARATUS AND METHOD

TECHNICAL FIELD

This invention relates to improvements in respiratory apparatus and to methods of ventilating patients generally, and neo-natal patients in particular.

BACKGROUND ART

The invention has application in the treatment of all classes of patients who require ventilation. The most difficult among those classes to treat is the new-born and, among the new-borns, the premature infant suffering from hyaline membrance disease, a condition in which the lungs are stiff and resist inflation. Lung capacity in such an infant may be no more than five cubic centimeters. In some cases the prescribed respiration rate is as high as 150 and even 180 cycles per minute. To provide a method and apparatus which is both suited to such an application and which is feasible in practice has proven to be a difficult problem.

The difficulty arises from the fact that the care needs of individual infants may differ widely both in the matter of ventilation and in respect of treatment for other conditions. The difficulty arises also from the fact that it is not possible to standardize the physical environment in which the infact and the respiratory apparatus are disposed. In practice, the distance from infant to ventilator is not uniform, even in the same hospital, and ambient temperatures differ and, of course, the characteristics of the commercially available ventilators and humidifiers and heaters and incubators and other enclosures vary greatly. An improvement that is to provide a real and available benefit to infants requiring ventilation must be universal in the sense that it must be compatible with a wide range of physical environments.

The invention utilizes, or is used in conjunction with, any of the commercially available ventilators and tracheal tubes. Almost all tracheal tubes are single lumen tubes. Respiratory gas is inspired and expired along the same passageway. No attempt is made to connect the tracheal tube alternately to a supply circuit and an exhaust circuit. A less dangerous practice is to control respiration by controlling pressure in a "respiratory" space to which the tracheal tube's supply end is exposed. Most of the available ventilators are equipped to supply pressurized respiratory gas to that "respiratory" space and to increase its pressure, and they are equipped to reduce its pressure by withdrawing gas or by permitting gas to escape from that space. Control of pressure reduction is accomplished at the ventilator to ensure control of the frequency of pressure change, and, therefore, respiration rate, and to ensure control of the magnitude of pressure and pressure change. To facilitate such pressure control, it is common to measure pressure at said space at the opening of the tracheal tube and to adjust supply pressure, flow rate, and removal rate at the ventilator.

Gas is very compressible, and the consequence of that quality and of viscous friction along the gas flowpath is to make it difficult to alter pressure rapidly in the respiratory space. The degree of difficulty increases with the volume and hence length of the flowpath from the ventilator to the respiratory space and back to the ventilator, and it increases with respiration rate. In any given instance, the flow resistance and volume can be reduced by shortening the flowpath. A nurse or respiratory therapist does that by selecting the shortest practical length of the supply and exhaust conduits. That having been done, volume can be reduced by selecting conduits of smaller cross-sectional area, but that increases flow resistance. Conversely, selecting a larger conduit reduces resistance but increases volume.

Volume is important because it and compressibility determine compliance, and compliance is manifested out of time phase with pressure whereas resistance is manifested in phase with pressure. The result is that it becomes impossible in a practical system to reduce pressure to atmospheric pressure at an intermediate point along the gas flowpath when the pressure is to be cycled at a relatively high rate. That translates into inability to achieve maximum practical exhalation in ventaliting patients.

The difficulty can be overcome in part by decreasing flow conduit size to reduce volume and compliance. That increases resistance, but the effect of increased resistance is overcome by the application of higher pressure to achieve higher flow rates. However, the increased pressure can result in dangerously high pressure peaks at the respiration point. An alternative is to apply suction at the exhaust end of the flow circuit. That can be dangerous, too. Negative pressure at the respiration point can result in collapsed lungs and, when suction is employed, it is usually machine controlled, manually adjustable and continually monitored.

The invention provides a very practical and effective solution to these problems.

DISCLOSURE OF INVENTION

It is an object of the invention to provide an improved method and apparatus for use in ventilating patients. An element in that improvement is a modification of the flow resistance and compliance relationship at the respiration junction at which the patient is connected to the supply and exhaust circuits. More particularly, the invention employs aspiration to reduce pressure at the respiration junction more rapidly than it would otherwise occur. Aspiration is accomplished in the preferred embodiment with increased flow volume rather than mere increased flow velocity. That feature permits more rapid pressure increase at the respiration junction to the end that pressure at the respiration junction varies less sinusoidally and more like a square wave.

Other features of the invention also involve control of flow, and respiration junction pressure, by altering or by providing greater uniformity in the volume and resistance of the flow circuit at points other than the respiration junction. It is a feature, for example, to place the pressure relief valve immediately downstream from the respiration junction to alter the effective ratio of compliance to resistance at the exhaust side of the system. Another feature is to house the supply conduit inside the exhaust conduit whereby to insulate the supply conduit in significant degree from ambient temperatures.

These and other features and advantages of the invention which will become apparent, can be understood more readily when considered in relation to a specific embodiment. The preferred embodiments of the invention are shown in the forms selected for illustration in the accompanying drawing.

BRIEF DESCRIPTION OF THE DRAWINGS

In the drawings:

FIG. 1 is a schematic drawing of a preferred form of the invention;

FIG. 2 is a cross-sectional view taken on line 2—2 of FIG. 3 of one preferred form of respiratory junction structure;

FIG. 3 is a cross-sectional view taken on line 3—3 of FIG. 2;

FIG. 4 is a partly schematic drawing of another preferred form of the invention;

FIG. 5 is a partly schematic, cross-sectional view of a water trap, coaxial flow conduit and a different preferred form of respiratory junction structure such as may be employed in the system of FIG. 4;

FIG. 6 is a cross-sectional view taken on line 6—6 of FIG. 5; and

FIG. 7 is a graph describing the operation of FIGS. 1 and 4 with prior art apparatus.

DESCRIPTION OF THE PREFERRED EMBODIMENT

FIG. 1 illustrates the application of one of the primary features of the invention to a conventional ventilation system. The system which is generally designated 10 includes a ventilator 12 which is shown as a block to indicate that it is one of a number of commercially available standard ventilators whose function is to ventilate a patient by alternately supplying pressurized gas to, and by receiving exhausted gas from, a tube which is inserted in the patient's trachea. A schematic representation of the tracheal tube is designated 14. Its lower end 16 is inserted into the patient's throat, and its input and outlet end 18 is coupled to a respiratory chamber or cavity 20. The cavity is contained within a housing 22. In preferred form that housing is formed with an inlet port 24, an outlet port 26, a pressure measuring port 28, and a temperature measuring port 30, in addition to the respiration or patient port to which the end 18 of the tracheal tube 14 is fitted.

The ventilator is connected by a supply conduit 30 to inlet port 24. The conduit 30 includes a condensation trap 32. Another condensation trap 34 is included in the expiratory or return conduit 36 which extends from the outlet port 26 to the ventilator. The ventilator supplies respiratory gas, under pressure, through the chamber 20 by conduit 30. The pressure in the respiratory chamber 20 rises to force gas into the patient's lungs by closing off the outlet, within the ventilator 12 of the expiratory conduit 36. To permit or to induce exhalation, the pressure in chamber 20 is reduced by opening the end of outlet conduit 36 to atmosphere within the ventilator 12. In some cases expiration is induced by applying suction to the end of conduit 36.

Most ventilators incorporate feedback control systems by which to maintain the temperature of the respiratory gas supply at a selected value. Temperature at the chamber 20 is sensed by a sensor at port 30, and it sends a signal to the ventilator 12 by line 40. Pressure, too, is controlled by a feedback system. The pressure in the chamber 20 is sensed at the ventilator 12 through a pressure sensing conduit 42 which opens to the chamber 20 at port 28.

Thus far described, the system of FIG. 1 corresponds to prior art systems. What is different is the inclusion of a means for aspirating gas from chamber 20 at the end of the inspiration portion of each breathing cycle. The affect of aspiration is to reduce the pressure in the chamber 20 more rapidly than would otherwise occur, and to lower the pressure within the patient's lungs to a value closer to zero guage pressure than would otherwise occur at high respiration rates.

In practice, chamber 22 is located immediately adjacent the patient. Ordinarily, that is directly at the end of the tracheal tube. The ventilator 12 may be located several feet away so that the total length of each of inspiratory conduits 31 and 30 and expiratory conduits 36 and 33 may be three or five feet long. The respiratory gas is humidified and heated to a temperature above room temperature whereby condensation is likely to occur within the inspiratory conduit 30. It is the function of the trap 32 to catch and to permit removal of the condensate. While the temperature of the exhaust gas in conduit 36 is somewhat lower, its temperature will exceed ambient room temperature, and the exhaust gas is likely to be even more humid than the inlet gas. Accordingly, condensation is expected in conduit 36 and it is the function of trap 34 to catch that condensate and to permit its removal.

The system volume includes the internal volume of the two condensate traps 32 and 34, the internal volume of as much as six to ten feet of the conduits 30, 31, 33 and 36, the volume of the respiratory chamber 20, and the volume of the tracheal tube 14 and the patient's lungs. The gas is pressurized to a value only a little above atmospheric pressure. It is very compressible. Both the inspiratory circuit and the expiratory circuit exhibit a relatively high value of compliance. In addition, those circuits offer resistance to gas flow, and resistance and compliance are inversely related. An increase in supply and exhaust conduit cross-sectional area to decrease resistance results in an increase in volume and, thus, an increase in total compliance. Conversely, reduction of volume to reduce compliance results in an increase in resistance. The back pressure that is exhibited as an incident to gas flow is exhibited in time phase with the pressure that causes that flow. On the other hand, back pressure, occasioned by the compliance of the system occurs out of time phase with the gas flow and the pressure that causes it. The result is that the exhaust circuit cannot be exhausted to atmospheric pressure and the pressure in chamber 20 cannot be reduced to atmospheric pressure, before the respiration chamber must be repressurized for the infant's next breath at the higher respiration rates. Thus, in practice, at the pressures and flow rates required for ventilation of the patient, is not possible to reduce the pressure within the chamber 20 to atmospheric pressure in the conventional system arrangement. In the terminology of the respiratory therapist, it is not possible to inadvertently eliminate PEEP (positive end expiratory pressure). It is one feature of the invention to eliminate or reduce that problem by aspirating the gas from the respiratory chamber at the beginning of the exhalation phase of each respiratory cycle and continuing for the duration of the exhalation period.

In the preferred form, the invention employs a restriction at the inlet space port of the respiratory housing or coupler. The restriction forces an increase in gas velocity as it emerges into the respiratory cavity. Lest the restriction limit the volume of incoming gas, thereby slowing the increase in pressurization of the respiratory cavity at the beginning of each inspiration, the supply pressure is increased whereby to increase flow volume. To prevent that increase in volume from simply filling and pressurizing the respiration cavity 20, rather than to aspirate gas from the cavity, the high velocity stream of inlet gas is directed into the outlet port of the respiration cavity. A preferred structure for achieving that result is shown in FIGS. 2 and 3. The housing 22 includes a flat upper wall 50 which is visible in FIG. 2. It includes a flat lower wall 52 which is visible in FIGS. 2 and 3, and it includes a cylindrical side wall 54 which is also visible in both figures. The housing is called a connector because each of its five ports opens to the interior of a respectively associated integrally formed cylindrical sleeve. Four of the sleeves have their axes in a common plane which is parallel and coincident, or nearly so, with the midplane through the cavity perpendicular to its central axis. Sleeve 56 opens to the inlet port, and sleeve 58 opens to the outlet port of the cavity. The axes of those two ports are coincident and parallel to the axes of sleeves 60 and 62 which are also coincident. A temperature sensor 64 is shown to be inserted in the sleeve 60 with its sensor 66 exposed in the respiratory cavity. Pressure is sensed through the small diameter lumen of a pressure sensing tube 68 whose end is held in the respiratory cavity by a fitting which is inserted into the sleeve 62. Thus, sleeve 60 opens to the port numbered 28 in FIG. 1, and sleeve 62 opens to the port numbered 30 in FIG. 1.

A flow restrictor 70 is shown to be inserted into the sleeve 56 at inlet port 24 as indicated in FIG. 1 and as shown in FIGS. 2 and 3. That restrictor is generally cylindrical over an initial portion of its length, and then in a region 72 is tapered to smaller diameter. End 74 is cylindrical and has reduced diameter. The outlet end of the restrictor is positioned approximately midway across the respiratory cavity as best shown in FIGS. 2 and 3. The outlet of the restrictor is pointed to direct flow into port 26 and sleeve 58. It is sleeve 58 that is connected to the exhaust conduit 36 of FIG. 1, and it is restrictor 70 that is connected to the inlet conduit 30 in FIG. 1. In this embodiment, the fifth port, the breathing or respiration port 76, has a diameter almost as large as the diameter of the respiratory cavity itself whereby to accommodate the fittings and couplers by which the tracheal tube is connected to the connector 22. The sleeve 76 extends in a direction perpendicular to the plane that contains the other four connection sleeves and is coincident with the axis of the respiratory cavity.

A conventional ventilator and humidifier is shown schematically in FIG. 4 where it is numbered 100, not because it is different than the ventilator of FIG. 1 but because it can be different in the details of its operation. The ventilator 100 includes a means 102, here shown as a box marked "PRES" for pressure, and a means 103 shown as a box marked "HUMID" for humidifier, for supplying a continuous flow of pressure limited respiratory gas to a supply conduit 104. The ventilator 100 also includes a means for permitting respiratory and exhaust gasses to flow from outlet line 106 to atmosphere. That means includes the normally closed valve 108 which is actuated by an actuator 110 represented by the block labelled "ACTU" in FIG. 4. The means for removing or permitting the removal of supply and exhaust gas from outlet conduit 106 may include a means 112 for employing suction to accomplish that task. Accordingly, a means 112 is represented by a block labelled "SUCTION" in FIG. 4. As in the case of ventilator 12 of FIG. 1, the ventilator 100 includes feedback systems permitting control in view of the pressure and temperature measured at the respiration chamber 114. Pressure information is conducted to the ventilator by a pressure line 116, and temperature information is transmitted to the ventilator by electrical line 118. The term "tracheal tube" is intended to designate both a tracheal tube and an endotracheal tube. Such a tube 120 is shown connected to the respiratory chamber 114. The chamber 114 includes an inlet port in which a flow restrictor 122 is disposed. That restrictor is similar to the restrictor 70 of FIGS. 1, 2 and 3.

In the FIG. 4 embodiment, the inspiratory conduit is housed within the expiratory conduit. This coaxial arrangement minimizes the heat transfer from the respiratory gas to atmosphere. Because of that, far less condensate can be expected in the inspiratory line, and the embodiment shown does not include a condensate trap at the inspiratory side of the circuit. A trap 126 is included in the expiratory conduit at the ventilator end of the coaxial section 128 of the two conduits.

In addition to having a coaxial flow conduit, this embodiment of the invention differs from the one shown in FIG. 1 in that it includes a flow control valve in the expiratory circuit immediately downstream from the respiratory cavity 114. The valve 130 is controlled by a valve controller 132 whose operation is coordinated with operation of the ventilator 100 using electrical or pneumatic signals transmitted by line 134 which interconnects the controller 132 and the ventilator.

The valve 130 and valve controller 132 perform substantially the same function that is performed by the valve 108 and the actuator 110 of the ventilator 100. That is, valve 130 is closed so that the respiratory cavity 114 will be pressurized, and gas will be supplied to the tracheal tube 120, as a consequence of the flow of supply gas to the respiratory cavity through the restriction 122. Thus, valve 130 is closed to initiate the inhalation portion of the respiratory cycle. At the end of the inhalation phase, when expiration is to begin, the valve 130 is opened to permit gas to escape from the chamber 114 whereby to reduce chamber pressure and permit or induce exhalation. The flow restrictor 122 has its flow directed to the outlet port 138 to provide the aspiration action described in connection with the apparatus of FIGS. 2 and 3. Valve 108 in the ventilator 100 is operated to permit flow from the expiratory conduit 106 when the valve 130 is opened either by being kept open or by being operated in a coordinated fashion with the valve 130.

The effect of placing the pressure relief valve 130 immediately adjacent to the respiratory cavity 114 is to reduce the compliance associated with the expiratory circuit so that only the resistance of the inspiratory circuit need be taken into account. Placing the valve at this point permits the use of the coaxial flow line arrangement section 128 notwithstanding that the volume of the expiratory portion of the conduit is substantially greater than that of the expiratory line 36 in FIG. 1. The use of the larger area line results in a reduction of downstream friction which is an additional aid to rapid reduction of pressure to atmospheric value in the chamber 114 during the exhalation phase.

The inclusion of the additional valve 130 permits the use of suction to evacuate the expiratory line with a greater degree of safety than would otherwise be experienced. Thus, by operating the valve 108 so that the expiratory line 106 is substantially exhausted of gas prior to the opening of valve 130, reduction of pressure in chamber 114 can be accomplished very rapidly. Further, the time required to build up pressure in chamber 114 can be reduced because the chamber 114 can be filled without need to fill the whole volume of the expiratory line 128.

A preferred form of water trap and coaxial flow conduit and a preferred form of respiration coupler is illustrated in FIG. 5 and in FIG. 6.

In FIG. 5 the trap 126 comprises a cylindrical body having a clyindrical wall 150, a forward wall 152, and a rearward wall 154. There are three openings or ports by which communication is had to the interior of the trap. One of those ports is formed in the forward wall of the trap and coxmunicates with a sleeve 156. That sleeve forms part of the expiratory line 106 in FIG. 4. At the rear side of the trap an inlet port is surrounded by a large diameter sleeve 158. The outer wall 160 of the coaxial conduit 128 has its outlet end installed on the sleeve 158. The other end of the outer wall of the coaxial conduit is installed on one end of the cylindrical outer wall 162 of the respiratory flow line coupler 164. The other end of that coupler is closed by an end closure which serves both to seal the other end of the cylindrical housing 162 and to hold the diaphragm 170 of a pressure closed diaphragm valve. The valve seat is formed by the rim of one end of a cylindrical flow tube that is mounted coaxially within the outer wall 162 of coupler 164. The inner flow tube is numbered 172. Its axis is coincident with the axis of the outer wall 162. A flow restrictor 174, which is similar to the flow restrictor 70 in FIG. 1 and flow restrictor 122 in FIG. 4, is installed in the left end of flow tube 172 such that its axis is coincident with the axis of flow tube 172 whereby the outflow from the restrictor is directed at the diaphragm valve 170.

The flow restrictor 174 is coupled to the inner conduit 104 of the coaxial conduit section 128. The other end of the inner conduit 104 is coupled to a flow tube 180 which is carried by the forward wall 152 of the water trap 126. The flow tube 128 has its axis coincident with the axis of sleeve 158 to which the outer coaxial conduit wall 160 is attached and its diameter is less than that of sleeve 158.

In this embodiment there are three cylindrical sleeves that extend through the outer wall 162 of the coupling unit 164 and open to the interior of the central flow tube 172. One of those sleeves is numbered 182 and it is arranged to receive the temperature sensor. Another sleeve, visible in both FIGS. 5 and 6, extends downwardly in both figures, is numbered 184 and is the sleeve to which the tracheal tube is connected. The third sleeve is visible only in FIG. 6. It extends off to the left and is numbered 186. It is to this sleeve that the pressure sensing line 116 of FIG. 4 is connected. The opening in the sleeve 186 is visible in FIG. 5 as a circle. It appears immediately adjacent the end of flow restrictor 174.

The operation of the diaphragm valve 170 is controlled by controlling the pressure in the cavity 188 between the diaphragm and the end closure 168. The pressure in that cavity is controlled by pressure applied through passage 190 which, in FIG. 4, is connected to the valve controller 132.

In the case of FIG. 5, the respiratory chamber is formed by the portion of the flow tube 172 between the diaphragm 170 and the inner end of the flow restrictor 174, by that portion of the sleeve 182 which is not filled by the pressure sensor, and by the sleeve 184. The pressure in that chamber is controlled by the pressure of the respiratory gas supplied through line 163 and the restrictor 174. The pressure is reduced by being relieved through the valve 170. When the diaphragm valve is retracted away from the end of the flow tube 172, gas can flow out of the respiration chamber and the tracheal tube to flow into the portion of the coupling device 164 that surrounds the flow tube 172 and then through the outer portion of the coaxial conduit to the trap 126 and then out sleeve 156 to the ventilator. As in the previously described versions of the invention, the effective flow from the flow restrictor 174 into the portion of the flow tube 172 at the right of the sleeve 184 results in an aspiration of gas from the sleeve 184. A reduction of pressure occurs within that sleeve greater than would occur at high respiration rates without the restrictor and flow accelerator 174. Of course, when the respiration rate is lowered to what is considered a normal rate for humans, the requirement for the flow restrictor is removed. However, even when the restrictor is not employed, the operation of the entire system is improved by the incorporation of the pressure release valve immediately downstream from the respiratory cavity and by use of the coaxial flow line.

The configuration illustrated in FIG. 5 provides the advantage that the flow lines and the sensing lines do, or can easily be made to, extend in the same direction from the manifold 164 so that installation, adjustment, and support of the structure is greatly facilitated. Those several features are very important when considered in the light of the very small size and delicacy of the premature infant. The advantage afforded by this construction is made even more important by the fact that a variety of other structures are possible in the special enclosures in which premature infants are housed. Those advantages, of course, are not limited to the case in which the patient is a premature infant. Indeed, they are of advantage in the treatment of patients of all ages.

Another feature of the invention, and an advantage which is exhibited in each of the several structures shown in the drawings, is provided by the construction in which the outlet opening of the aspirator is positioned opposite from, and is directed into, an expiration port or passageway. Any condensation which appears in the inspiratory tube and escapes the condensation trap will be propelled in the aspirator across the respiration cavity into the outlet opening. Water particles will have a velocity approaching that of the gas as them emerge from the aspirator, and because of their greater weight and kinetic energy will be propelled across the cavity into the outlet passage whereby any opportunity for that moisture to reach the patient is minimized.

While the representation is only relative, the graphs in FIG. 6 will illustrate the effect of the invention. Time is plotted along the X axis in FIG. 7 from an earlier time at the left to a later time at the right. The pressure at the respiratory chamber end of the tracheal tube is represented on the abscissa of the graph. The dashed curve 194 depicts the pressure variation at the end of the tracheal tube at high respiration rates in the absence of the invention. It will be observed that the pressure rises and falls almost sinusoidially. The pressure is not reduced to zero during the expiration intervals. The peak pressure must reach a relatively high value to ensure that chamber pressure is high enough for the whole of the inspiration period to ensure adequate filling of the lungs. The ideal pressure time curve approaches a square wave. Pressure in such a wave would rise rapidly to a safe value less than the peak value of curve 194 and would remain at that level until the lungs were adequately filled. Thereafter, pressure would fall rapidly to zero so that the lungs could be exhausted in preparation for the next inhalation. The solid line in FIG. 7 represents the pressure variation with time that is achieved by incorporation of the aspirator of the invention. The solid line is numbered 196 for identification. The addition of the valve 130 in FIG. 4 and 170 in FIG. 5 provides an improvement in rise time and pressure release time as shown by the dotted line modification of solid curve 196. The improvement in rise time that can be achieved is represented by dotted line 198, and the improvement in pressure release time is depicted by dotted line 200.

Although we have shown and described certain specific embodiments of our invention, we are fully aware that many modifications thereof are possible. Our invention, therefore, is not to be restricted except insofar as is necessitated by the prior art.

We claim:

1. Respiratory apparatus for connection to a ventilator system such as to receive respiratory gas from said ventilator and to direct unused respiratory gas and exhaled gas back to said ventilator, said respiratory apparatus comprising:
   a housing defining a chamber;
   a gas inlet port in said housing opening to said chamber;
   a gas outlet port in said housing opening to said chamber;
   a respiratory port in said housing opening to said chamber;
   aspiration means for reducing the pressure in said chamber as an incident to an increase in the rate of flow into said chamber at said inlet port;
   an inlet flow conduit having one end connected to said inlet port;
   an outlet flow conduit having one end connected to said outlet port;
   said aspiration means being formed by a restriction at said inlet port which directs flow to said outlet port;
   cyclically operable valve means for alternately completing and closing a pathway for gas through said outlet port and said outlet flow conduit;
   said valve means comprising a valve disposed adjacent to said outlet port; and
   said inlet and outlet conduits being concentric, the inlet conduit being disposed within the outlet conduit, and which comprises means for interconnecting the outlet flow conduit to the outlet port such that the outlet conduit may encompass the inlet conduit.

2. Respiratory apparatus for connection to a ventilator system such as to receive respiratory gas from said ventilator and to direct unused respiratory gas and exhaled gas back to said ventilator, said respiratory apparatus comprising:
   a housing defining a chamber;
   a gas inlet port in said housing opening to said chamber;
   a gas outlet port in said housing opening to said chamber;
   a respiratory port in said housing opening to said chamber;
   aspiration means for reducing the pressure in said chamber as an incident to an increase in the rate of flow into said chamber at said inlet port;
   an inlet flow conduit having one end connected to said inlet port;
   an outlet flow conduit having one end connected to said outlet port;
   said aspiration means being formed by a restriction at said inlet port which directs flow to said outlet port;
   cyclically operable valve means for alternately completing and closing a pathway for gas through said outlet port and said outlet flow conduit;
   said valve means comprising a valve disposed adjacent to said outlet port; and
   further comprising means for opening and closing said valve at a rate exceeding one hundred cycles per minute.

3. Respiratory apparatus for connection to a ventilator system such as to receive respiratory gas from said ventilator and to direct unused respiratory gas and exhaled gas back to said ventilator, said respiratory apparatus comprising:
   a housing defining a chamber;
   a gas inlet port in said housing opening to said chamber;
   a gas outlet port in said housing opening to said chamber;
   a respiratory port in said housing opening to said chamber;
   means for thermally insulating said chamber comprising a tubing communication with said outlet port and encompassing said chamber and in which tubing said gas inlet port and said gas outlet port and said respiratory port are contained, and for interconnecting said output port with the interior of said encompassing tubing, and conduit means connected to said respiratory port and extending through said tubing to the exterior thereof for connection to a patient;
   aspiration means for reducing the pressure in said chamber as an incident to an increase in the rate of flow into said chamber at said inlet port; and
   a valve connected in series with, adjacent to, and downstream from said outlet port, and being capable of permitting and interrupting a flow of gas from said cavity via said outlet port.

4. The invention defined in claim 3 which further comprises a second valve connected in series with and downstream from said first mentioned valve and said outlet port, and being capable of permitting and interrupting a flow of gas from said cavity via said outlet port.

5. The invention defined in claim 3 in which said housing comprises first and second tubular elements intersecting one another at an angle to form a chamber at their intersection, the gas inlet port and the gas outlet port being defined at the intersection by portions of said first tubular member;
   a third tubular member encompassing said first tubular element and having its axis substantially coincident with the axis of said first tubular element.

* * * * *